(12) United States Patent
Lau et al.

(10) Patent No.: US 6,689,159 B2
(45) Date of Patent: Feb. 10, 2004

(54) EXPANDABLE STENTS AND METHOD FOR MAKING SAME

(75) Inventors: Lilip Lau, Sunnyvale, CA (US); William M. Hartigan, Fremont, CA (US); John J. Frantzen, Copperopolis, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/427,796

(22) Filed: May 1, 2003

(65) Prior Publication Data

US 2003/0195615 A1 Oct. 16, 2003

Related U.S. Application Data

(62) Division of application No. 09/779,078, filed on Feb. 8, 2001, now Pat. No. 6,596,022, which is a division of application No. 09/561,098, filed on Apr. 28, 2000, now Pat. No. 6,309,412, which is a division of application No. 09/135,222, filed on Aug. 17, 1998, now Pat. No. 6,056,776, which is a division of application No. 09/055,582, filed on Apr. 6, 1998, now Pat. No. 6,066,168, which is a division of application No. 08/783,097, filed on Jan. 14, 1997, now Pat. No. 5,735,893, which is a division of application No. 08/556,516, filed on Nov. 13, 1995, now Pat. No. 5,603,721, which is a division of application No. 08/281,790, filed on Jul. 28, 1994, now Pat. No. 5,514,154, which is a continuation-in-part of application No. 08/164,986, filed on Dec. 9, 1993, now abandoned, which is a continuation of application No. 07/783,558, filed on Oct. 28, 1991, now abandoned.

(51) Int. Cl.$^7$ ................................................ A61F 2/06
(52) U.S. Cl. ..................................................... 623/1.16
(58) Field of Search ...................... 623/1.15, 1.16–1.12

(56) References Cited

U.S. PATENT DOCUMENTS

| | | | |
|---|---|---|---|
| 2,701,559 | A | 2/1955 | Cooper |
| 3,105,492 | A | 10/1963 | Jeckel |
| 3,657,744 | A | 4/1972 | Ersek |
| 3,868,956 | A | 3/1975 | Alfidi et al. |
| 3,993,078 | A | 11/1976 | Bergentz et al. |

(List continued on next page.)

FOREIGN PATENT DOCUMENTS

| | | |
|---|---|---|
| DE | 36 40 745 A1 | 6/1987 |
| DE | 38 23 060 A1 | 1/1989 |

(List continued on next page.)

OTHER PUBLICATIONS

Dotter, Charles T., *Transluminally Placed Coilspring Endarterial Tube Grafts, Investigative Radiology*, pp. 329–332, Sep./Oct. 1969.

(List continued on next page.)

*Primary Examiner*—Corrine McDermott
*Assistant Examiner*—Suzette J. Jackson
(74) *Attorney, Agent, or Firm*—Fulwider Patton Lee & Utecht, LLP

(57) ABSTRACT

The invention is directed to an expandable stent for implantation in a body lumen, such as an artery, and a method for making it from a single length of tubing. The stent consists of a plurality of radially expandable cylindrical elements generally aligned on a common axis and interconnected by one or more interconnective elements. The individual radially expandable cylindrical elements consist of ribbon-like material disposed in an undulating pattern. Portions of the expanded stent project outwardly into engagement with the vessel wall to more securely attach the stent.

9 Claims, 4 Drawing Sheets

U.S. PATENT DOCUMENTS

| | | |
|---|---|---|
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,665,918 A | 5/1987 | Garza et al. |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger |
| 4,768,507 A | 9/1988 | Fischell et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsly et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,397 A | 9/1993 | Barath et al. |
| 5,242,399 A | 9/1993 | Lau et al. |
| 5,242,452 A | 9/1993 | Inoue |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,426 A | 9/1994 | Lau et al. |
| 5,354,308 A | 10/1994 | Simon et al. |
| 5,356,433 A | 10/1994 | Rowland et al. |
| 5,360,401 A | 11/1994 | Turnland |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,421,955 A | 6/1995 | Lau |
| 5,423,745 A | 6/1995 | Todd et al. |
| 5,423,885 A | 6/1995 | Williams |
| 5,445,646 A | 8/1995 | Euteneuer et al. |
| 5,449,373 A * | 9/1995 | Pinchasik et al. ............ 606/198 |
| 5,456,694 A | 10/1995 | Marin et al. |
| 5,458,615 A | 10/1995 | Klemm et al. |
| 5,476,476 A | 12/1995 | Hillstead |
| 5,484,449 A | 1/1996 | Amundson et al. |
| 5,507,768 A | 4/1996 | Lau et al. |
| 5,514,154 A | 5/1996 | Lau et al. |
| 5,545,132 A | 8/1996 | Fagan et al. |
| 5,571,135 A | 11/1996 | Fraser et al. |
| 5,591,197 A * | 1/1997 | Orth et al. ................. 623/1.16 |
| 5,603,721 A | 2/1997 | Lau et al. |

| | | | |
|---|---|---|---|
| 5,626,604 A | | 5/1997 | Cottone et al. |
| 5,649,952 A | * | 7/1997 | Lam .......................... 623/1.15 |
| 5,653,690 A | | 8/1997 | Booth et al. |
| 5,653,691 A | | 8/1997 | Rupp et al. |
| 5,653,727 A | | 8/1997 | Wiktor |
| 5,716,396 A | | 2/1998 | Williams |
| 5,720,726 A | | 2/1998 | Marcadis et al. |
| 5,733,303 A | | 3/1998 | Israel |
| 5,733,325 A | | 3/1998 | Robinson |
| 5,735,893 A | | 4/1998 | Lau et al. |
| 5,782,855 A | | 7/1998 | Lau et al. |
| 5,800,521 A | | 9/1998 | Orth |
| 5,810,871 A | | 9/1998 | Tuckey et al. |
| 5,817,152 A | | 10/1998 | Birdsall et al. |
| 5,830,217 A | | 11/1998 | Ryan |
| 5,836,965 A | | 11/1998 | Jendersee et al. |
| 5,843,164 A | * | 12/1998 | Frantzen et al. ........... 623/1.16 |
| 5,893,852 A | | 4/1999 | Morales |
| 5,902,332 A | | 5/1999 | Schatz |
| 5,984,964 A | | 11/1999 | Roberts et al. |
| 5,997,468 A | | 12/1999 | Wolff et al. |
| 6,030,413 A | | 2/2000 | Lazarus |
| 6,146,358 A | | 11/2000 | Rowe |

FOREIGN PATENT DOCUMENTS

| | | |
|---|---|---|
| EP | 0 517 075 | 12/1992 |
| EP | 0 540 290 A2 | 5/1993 |
| EP | 0 541 443 A1 | 5/1993 |
| FR | 2 677 872 | 12/1992 |
| GB | 2 070 490 A | 9/1981 |
| GB | 2 135 585 A | 9/1984 |
| JP | 58-501458 | 9/1983 |
| JP | 62-213762 | 9/1987 |
| JP | 62-231657 | 10/1987 |
| JP | 62-235496 | 10/1987 |
| JP | 63-21464 | 9/1988 |
| JP | 63-246178 | 10/1988 |
| JP | 64-83685 | 3/1989 |
| JP | 1-299550 | 12/1989 |
| JP | 2-174859 | 7/1990 |
| JP | 2-255157 | 10/1990 |
| JP | 3-9745 | 1/1991 |
| JP | 3-9746 | 1/1991 |
| JP | 3-57465 | 3/1991 |
| JP | 3-151983 | 6/1991 |
| JP | 4-25755 | 2/1992 |
| WO | WO 89/01798 | 3/1989 |
| WO | WO 89/08433 | 9/1989 |
| WO | WO 91/07139 | 5/1991 |
| WO | WO 92/06734 | 4/1992 |
| WO | WO 92/09246 | 6/1992 |

OTHER PUBLICATIONS

Rösch, J., M.D., et al., *Transjugular Intrahepatic Portacaval Shunt: An Experimental Work, The American Journal of Surgery*, pp. 588–592, vol. 121, May 1971.

Dotter, Charles T., *Transluminal Expandable Nitinol Coil Stent Grafting: Preliminary Report, Radiology Journal*, pp. 259–260, Apr. 1983.

Cragg, et al., *Non–Surgical Placement of Arterial Endoprostheses: A New Technique Using Nitinol Wire, Radiology Journal*, pp. 261–263, Apr. 1983.

Maass, et al., *Radiological Follow–Up of Transluminally Inserted Vascular Endoprostheses: An Experimental Study Using Expanding Spirals, Radiology Journal*, pp. 659–663, 1984.

70$^{th}$ *Scientific Assembly and Annual Meeting: Scientific Program, Radiology*, Washington, D.C., Nov. 25–30, 1984, special Edition, vol. 153(P).

C.R. Bard, *PE Plus Peripheral Balloon Dilatation Catheter*, C.R. Bard, Inc., Aug. 1985.

Wright, et al., *Percutaneous Endovascular Stents: An Experimental Evaluation, Radiology Journal*, pp. 69–72, 1985.

Charnsangavej, C., M.D., et al., *Endovascular Stent for Use in Aortic Dissection: An In Vitro Experiment, Radiology*, pp. 323–324, vol. 157, No. 2, Nov. 1985.

Palmaz, et al., *Expandable Intraluminal Graft: A Preliminary Study, Radiology Journal*, pp. 73–77, 1985.

72$^{nd}$ *Scientific Assembly and Annual Meeting: RSNA Scientific Program, Radiology*, Chicago: Nov. 30–Dec. 5, 1986, Special Edition, vol. 161(P).

Wallace, Michael J., et al., *Tracheobronchial Tree: Expandable Metallic Stents Used in Experimental and Clinical Applications (Work in Progress), Radiology*, pp. 309–312, vol. 158, Feb. 1986.

*Program: Day 2 (Nov. 18) The Radiological Society of North America, Radiology*, Chicago: Nov. 30–Dec. 5, 1986, Special Edition, vol. 161(P).

72$^{ND}$ *Scientific Assembly and Annual Meeting: RSNA Scientific Program, Radiology*, Chicago: Nov. 30–Dec. 5, 1986, Special Edition vol. 161(P).

Charnsangavej, Chuslip, M.D., et al., *Stenosis of the Venaq Cava: Preliminary Assessment of Treatment With Expandable Metallic Stents, Radiology*, pp. 295–298, vol. 161, Nov. 1986.

Duprat, et al., *Flexible Balloon–Expanded Stent for Small Vessels, Radiology Journal*, pp. 276–278, 1987.

Rösch, Josef, M.D., et al., *Experimental Intrahepatic Portacaval Anastomosis: Use of Expandable Gianturco Stents, Radiology*, pp. 481–485, vol. 162, Feb. 1987.

Rösch, Josef, M.D., et al., *Gianturco Expandable Stents in Experimental and Clinical Use*, paper presented at The Twelfth Annual Course on "Diagnostic Angiography and Interventional Radiology" Mar. 23–26, 1987 (Pittsburgh, Pennsylvania).

Finci, Leo, M.D., et al., *Percutaneous Transluminal Coronary Angioplasty of a Bifurcation Narrowing Using the Kissing Wire Monorail Balloon Technique, The American Journal of Cardiology*, Apr. 1987.

Lawrence, David D., Jr., M.D., et al., *Percutaneous Endovascular Graft: Experimental Evaluation, Radiology*, pp. 357–360, vol. 163, May 1987.

Rösch, Josef, M.D., et al., *Gianturco Expandable Wire Stents in the Treatment of Superior Vena Cava Syndrome Recurring After Maximum–Tolerance Radiation, Cancer*, pp. 1243–1246, vol. 60, Sep. 1987.

Bonzel, T., et al., *The Sliding Rail System (Monorail): Description of a New Technique for Intravascular Instrumentation and its Application to Coronary Angioplasty, Kardiologie*, Supplement 6, pp. 119–122 (1987).

Yoshioka, Tetsuya, et al., *Self–Expanding Endovascular Graft: An Experimental Study in Dogs, American Journal of Roentgeriology*, pp. 673–676, vol. 151, Oct. 1988.

Rösch, Josef, M.D., et al., *Modified Gianturco Expandable Wire Stents in Experimental and Clinical Use, Annales de Radiologie*, pp. 100–103, vol. 31, No. 2, 1988.

Yoshioka, et al. "*Development and Clinical Application of Biliary Endoprothesis Using Expandable Metallic Stents,*" *Japan Radiological Society*, 1988, vol. 48 No. 9, pp. 1183–1185. (with translation).

Yoshioka, et al. "*Self Expanding Endovascular Graft: An Experimental Study in Dogs,*" *American Journal of Roentgeriology*, 1988, vol. 151, pp. 673–676.

Mirich, et al. "*Percutaneously Placed Endovascular Grafts for Aoertic Aneurysms: Feasbility Study,*" *Radiology*, 1989, part 2, p1033–37.

Furui, Shigeru, M.D., et al., *Hepatic Inferior Vena Cava Obstruction: Treatment of Two Types with Gianturco Expandable Metallic Stents, Radiology*, pp. 665–670, Sep. 1990.

Kaltenbach, M., Prof. Dr., Abstracts, *Zeitschrift für Kardiologie*, Apr. 3, 1991 (German only).

van der Giessen, Willem J., et al., *Coronary Stenting With a New, Radiopaque Balloon–Expandable Endoprosthesis in Pigs, Circulation*, vol. 83, No. 5, pp. 93–149, May 1991.

Strupp, G. et al., *Clinical and Angiographic Short and Medium Term Results After Coronary Stenting, Zietschrift für Kardiologie*, Sep. 9, 1992 (German with English language summary).

Harrington, J.C., et al., *The Palmaz–Schatz Stent, Handbook of Cardiovascular Interventions/Vascular Interventions*, pp. 563–572 (Undated).

* cited by examiner

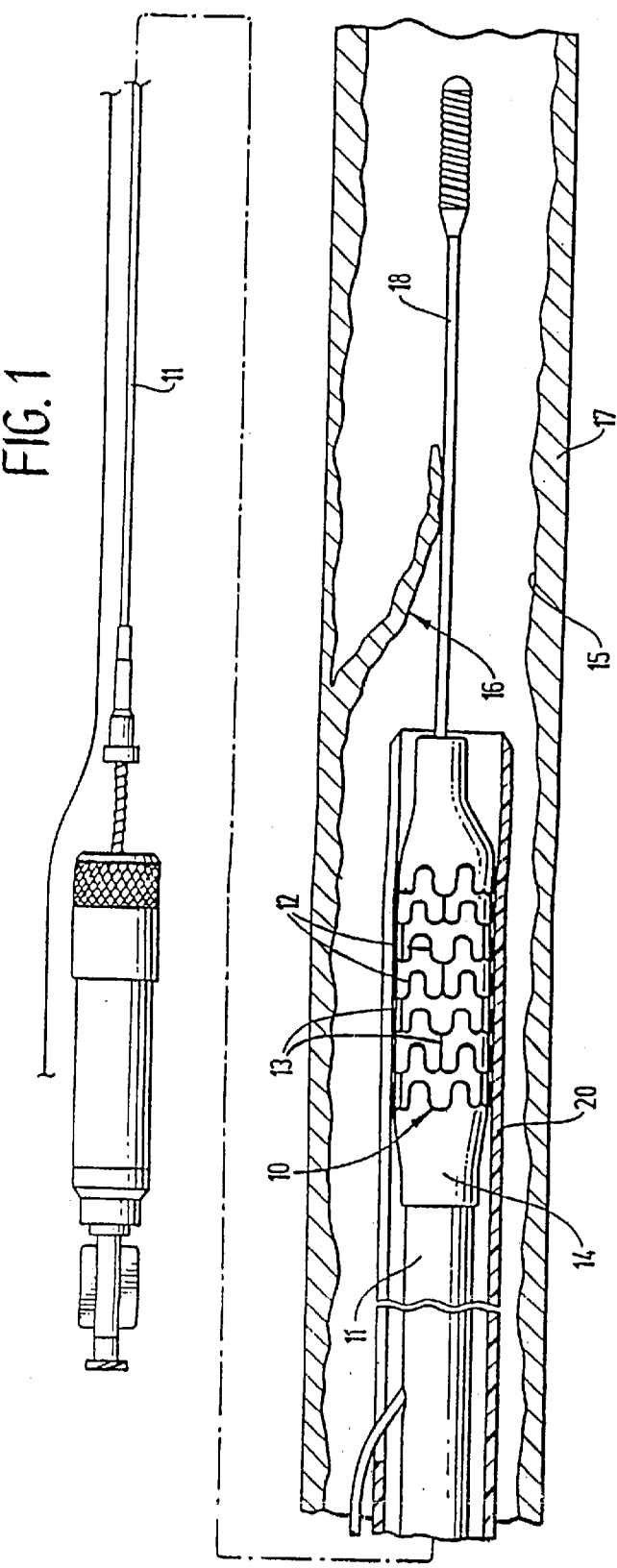
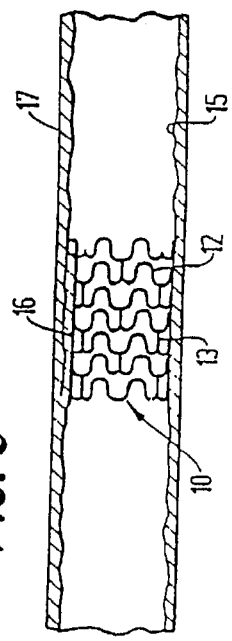
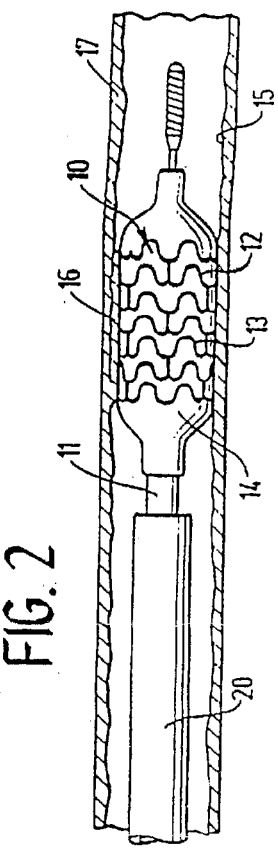

EXPANDABLE STENTS AND METHOD FOR MAKING SAME

RELATED APPLICATIONS

This application is a division of U.S. Ser. No. 09/779,078 filed Feb. 8, 2001 now U.S. Pat. No. 6,596,022, which is a division of U.S. Ser. No. 09/561,098 filed Apr. 28, 2000 now U.S. Pat. No. 6,309,412, which is a division of U.S. Ser. No. 09/135,222 filed Aug. 17, 1998 now U.S. Pat. No. 6,056,776, which is a division of U.S. Ser. No. 09/055,582 filed Apr. 6, 1998 now U.S. Pat. No. 6,066,168, which is a division of U.S. Ser. No. 08/783,097 filed Jan. 14, 1997, now U.S. Pat. No. 5,735,893, which is a division of U.S. Ser. No. 08/556,516, filed Nov. 13, 1995, now U.S. Pat. No. 5,603,721, now U.S. Pat. No. 5,603,721, which is a division of U.S. Ser. No. 08/281,790, filed Jul. 28, 1994, now U.S. Pat. No. 5,514,154, which is a continuation in part of U.S. Ser. No. 08/164,986 filed Dec. 9, 1993, now abandoned, which is a continuation of Ser. No. 07/783,558, filed Oct. 28, 1991, now abandoned.

BACKGROUND OF THE INVENTION

This invention relates to expandable endoprosthesis devices, generally called stents, which are adapted to be implanted into a patient's body lumen, such as blood vessel, to maintain the patency thereof. These devices are very useful in the treatment of atherosclerotic stenosis in blood vessels.

Stents are generally tubular-shaped devices which function to hold open a segment of a blood vessel or other anatomical lumen. They are particularly suitable for use to support and hold back a dissected arterial lining which can occlude the fluid passageway therethrough.

Further details of prior art stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); and U.S. Pat. No. 4,886,062 (Wiktor), which are hereby incorporated herein in their entirety by reference thereto.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery.

What has been needed and heretofore unavailable is a stent which has a high degree of flexibility so that it can be advanced through tortuous passageways and can be readily expanded and yet have the mechanical strength to hold open the body lumen into which it expanded. The present invention satisfies this need.

SUMMARY OF THE INVENTION

The present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein.

The stent of the invention generally includes a plurality of radially expandable cylindrical elements which are relatively independent in their ability to expand and to flex relative to one another. The individual radially expandable cylindrical elements of the stent are dimensioned so as to be longitudinally shorter than their own diameters. Interconnecting elements or struts extending between adjacent cylindrical elements provide increased stability and a preferable position to prevent warping of the stent upon the expansion thereof. The resulting stent structure is a series of radially expandable cylindrical elements which are spaced longitudinally close enough so that small dissections in the wall of a body lumen may be pressed back into position against the lumenal wall, but not so close as to compromise the longitudinal flexibilities of the stent. The individual cylindrical elements may rotate slightly relative to adjacent cylindrical elements without significant deformation, cumulatively giving a stent which is flexible along its length and about its longitudinal axis but is still very stiff in the radial direction in order to resist collapse.

The stent embodying features of the invention can be readily delivered to the desired lumenal location by mounting it on an expandable member of a delivery catheter, for example a balloon, and passing the catheter-stent assembly through the body lumen to the implantation site. A variety of means for securing the stent to the expandable member on the catheter for delivery to the desired location are available. It is presently preferred to compress the stent onto the balloon. Other means to secure the stent to the balloon include providing ridges or collars on the inflatable member to restrain lateral movement, or using bioresorbable temporary adhesives.

The presently preferred structure for the expandable cylindrical elements which form the stents of the present invention generally circumferential undulating pattern, e.g. serpentine. The transverse cross-section of the undulating component of the cylindrical element is relatively small and preferably has an apect ratio of about two to one to about 0.5 to one. A one to one apect ratio has been found particularly suitable. The open reticulated structure of the stent allows for the perfusion of blood over a large portion of the arterial wall which can improve the healing and repair of a damaged arterial lining.

The radial expansion of the expandable cylinder deforms the undulating pattern thereof similar to changes in a waveform which result from decreasing the waveform's amplitude and the frequency. Preferably, the undulating patterns of the individual cylindrical structures are in phase with each other in order to prevent the contraction of the stent along its length when it is expanded. The cylindrical structures of the stent are plastically deformed when expanded (except with NiTi alloys) so that the stent will remain in the expanded condition and therefore they must be sufficiently rigid when expanded to prevent the collapse thereof in use. During expansion of the stent, portions of the undulating pattern will tip outwardly resulting in projecting members on the outer surface of the expanded stent. These projecting members tip radially outwardly from the outer surface of the stent and embed in the vessel wall and help secure the expanded stent so that it does not move once it is implanted.

With superelastic NiTi alloys, the expansion occurs when the stress of compression is removed so as to allow the phase transformation from austenite back to martensite and as a result the expansion of the stent.

The elongated elements which interconnect adjacent cylindrical elements should have a transverse cross-section similar to the transverse dimensions of the undulating components of the expandable cylindrical elements. The interconnecting elements-may be formed in a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. Preferably, all of the interconnecting elements of a stent are joined at either the peaks or the valleys of the undulating structure of the cylindrical elements which for the stent. In this manner there is no shortening of the stent upon expansion.

The number and location of elements interconnecting adjacent cylindrical elements can be varied in order to develop the desired longitudinal flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

In a presently preferred embodiment of the invention the stent is conveniently and easily formed by coating stainless steel tubing with a material resistant to chemical etching, removing portions of the coating to expose portions of underlying tubing which are to be removed to develop the desired stent structure. The exposed portions of the tubing are removed by chemically etching from the tubing exterior leaving the coated portion of the tubing material in the desired pattern of the stent structure. The etching process develops smooth openings in the tubing wall without burrs or other artifacts which are characteristic of mechanical or laser machining processes in the small sized products contemplated. Moreover, a computer controlled laser patterning process to remove the chemical resistive coating makes photolithography technology adaptable to the manufacture of these small products. The forming of a mask in the extremely small sizes needed to make the small stents of the invention would be a most difficult task. A plurality of stents can be formed from one length of tubing by repeating the stent pattern and providing small webs or tabs to interconnect the stents. After the etching process, the stents can be separated by severing the small webs or tabs which connect them.

Other features and advantages of the present invention will become more apparent from the following detailed description of the invention. When taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery, pressing the damaged lining against the arterial wall.

FIG. 3 is an elevational view, partially in section showing the expanded stent within the artery after withdrawal of the delivery catheter.

DETAILED DESCRIPTION OF THE PREFERRED EMBODIMENTS

Figure 4:
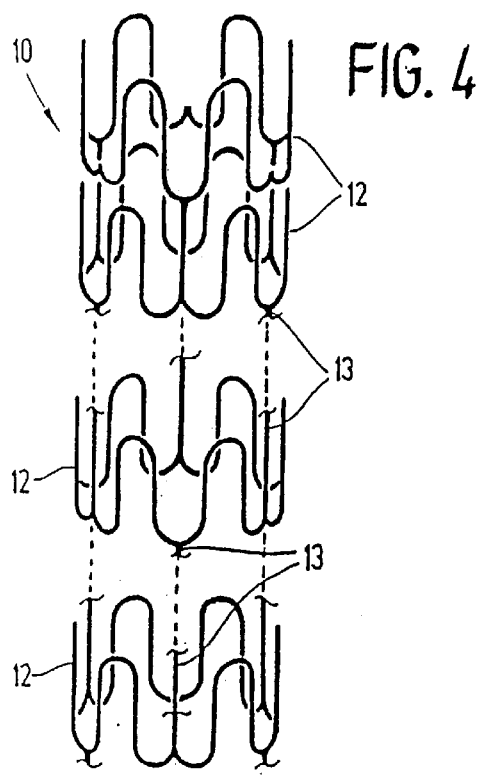
FIG. 4 is a perspective view of a stent embodying features of the invention in an unexpanded state, with one end of the stent being shown in an exploded view illustrate the details thereof.

FIG. 1 illustrates a stent 10 incorporating features of the invention which is mounted onto a delivery catheter 11. The stent generally comprises a plurality of radially expandable cylindrical elements 12 disposed generally coaxially and interconnected by elements 13 disposed between adjacent cylindrical elements. The delivery catheter 11 has an expandable portion or balloon 14 for expanding of the stent 10 within an artery 15. The artery 15, as shown in FIG. 1 has a dissected lining 16 which has occluded a portion of the arterial passageway.

The delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is compressed onto the balloon. A retractable protective delivery sleeve 20 as described in copending application Ser. No. 07/647,464 filed on Apr. 25, 1990 and entitled STENT DELIVERY SYSTEM may be provided to further ensure that the stent stays in place on the expandable portion of the delivery catheter 11 and prevent abrasion of the body lumen by the open surface of the stent 20 during delivery to the desired arterial location. Other means for securing the stent 10 onto the balloon 14 may also be used, such as providing collars or ridges on the ends of the working portion, i.e. the cylindrical portion, of the balloon.

Each radially expandable cylindrical element 12 of the stent 10 may be independently expanded. Therefore, the balloon 14 may be provided with an inflated shape other than cylindrical, e.g. tapered, to facilitate implantation of the stent 10 in a variety of body lumen shapes.

In a preferred embodiment, the delivery of the stent 10 is accomplished in the following manner. The stent 10 is first mounted onto the inflatable balloon 14 on the distal extremity of the delivery catheter 11. The balloon 14 is slightly inflated to secure the stent 10 onto the exterior of the balloon. The catheter-stent assembly is introduced within the patient's vasculature in a conventional Seldinger technique through a guiding catheter (not shown). A guidewire 18 is disposed across the damaged arterial section with the detached or dissected lining 16 and then the catheter-stent assembly is advanced over a guidewire 18 within the artery 15 until the stent 10 is directly under the detached lining 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent 10 from elongated tubular member, the undulating component of the cylindrical elements of the stent 10 is relatively flat in transverse cross-section, so that when the stent is expanded, the cylindrical elements are pressed into the wall of the artery 15 and as a result do not interfere with the blood flow through the artery 15. The cylindrical elements 12 of stent 10 which are pressed into the wall of the artery 15 will eventually be covered with endothelial cell growth which further minimizes blood flow interference. The undulating portion of the cylindrical sections 12 provide good tacking characteristics to prevent stent movement within the artery. Furthermore, the closely spaced cylindrical elements 12 at regular intervals provide uniform support for the wall of the artery 15, and consequently are well adapted to tack up and hold in place small flaps or dissections in the wall of the artery 15 as illustrated in FIGS. 2 and 3.

FIG. 4 is an enlarged perspective view of the stent 10 shown in FIG. 1 with one end of the stent shown in an exploded view to illustrate in greater detail the placement of interconnecting elements 13 between adjacent radially expandable cylindrical elements 12. Each pair of the interconnecting elements 13 on one side of a cylindrical element 12 are preferably placed to achieve maximum flexibility for a stent. In the embodiment shown in FIG. 4 the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible, and several examples are illustrated schematically in FIGS. 7–10. However, as previously mentioned, all of the interconnecting elements of an individual stent should be secured to either the peaks or valleys of the undulating structural elements in order to prevent shortening of the stent during the expansion thereof.

Figure 10:
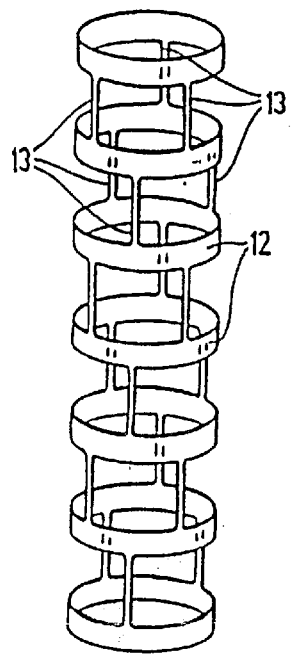

FIG. 10 illustrates a stent of the present invention wherein three interconnecting elements 12 are disposed between radially expandable cylindrical elements 11. The interconnecting elements 12 are distributed radially around the circumference of the stent at a 120-degree spacing. Disposing four or more interconnecting elements 13 between adjacent cylindrical elements 12 will generally give rise to the same considerations discussed above for two and three interconnecting elements.

Figure 11:
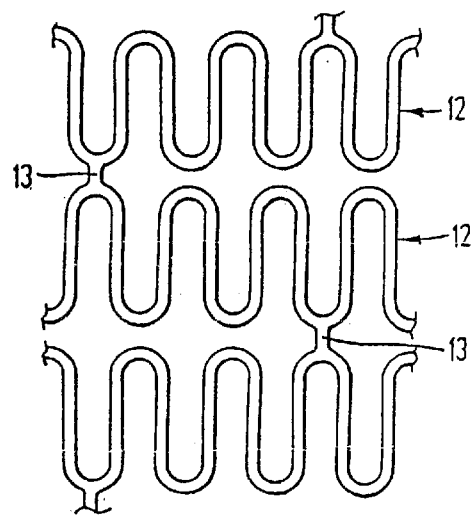
FIG. 11 is a plan view of a flattened section of a stent illustrating an alternate undulating pattern in the expandable cylindrical elements of the stent which are out of phase.
Figure 12:
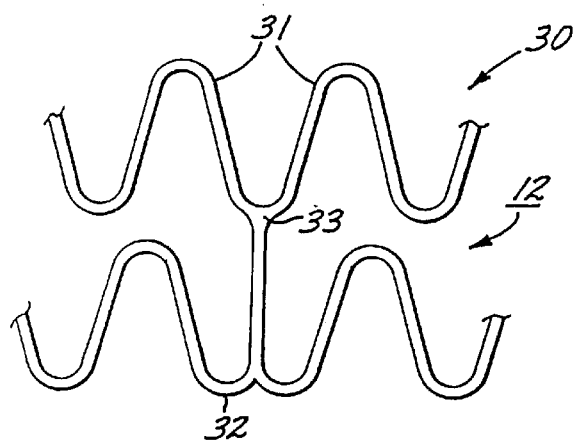
FIG. 12 is an enlarged partial view of the stent of FIG. 5 with the various members slightly expanded.

The properties of the stent 10 may also be varied by alteration of the undulating pattern of the cylindrical elements 13. FIG. 11 illustrates an alternative stent structure in which the cylindrical elements are in serpentine patterns but out of phase with adjacent cylindrical elements. The particular pattern and how many undulations per unit of length around the circumference of the cylindrical element 13, or the amplitude of the undulations, are chosen to fill particular mechanical requirements for the stent such as radial stiffness.

Figure 5:
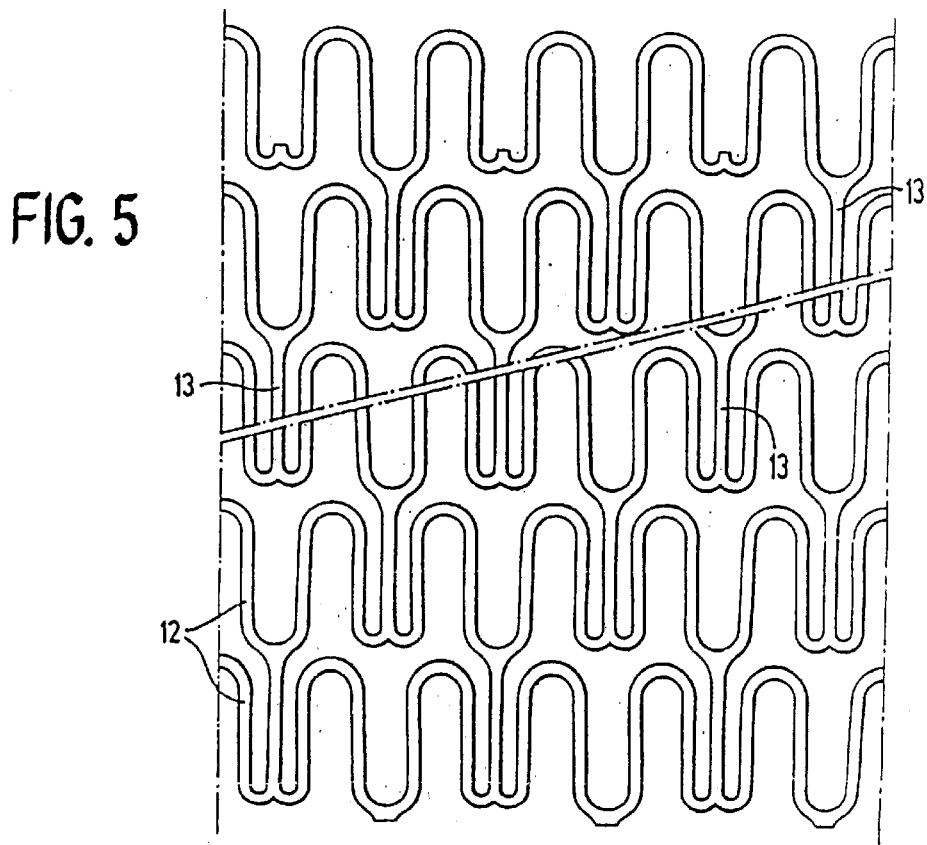
FIG. 5 is a plan view of a flattened section of a stent of the invention which illustrates the undulating pattern of the stent shown in FIG. 4.
Figure 7:
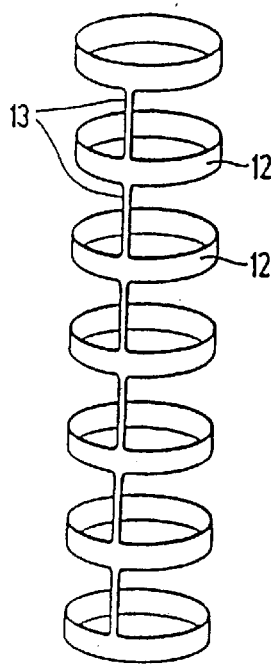
FIGS. 7 through 10 are perspective views schematically illustrating various configurations of interconnective element placement between the radially expandable cylindrical elements of the stent.
Figure 8:
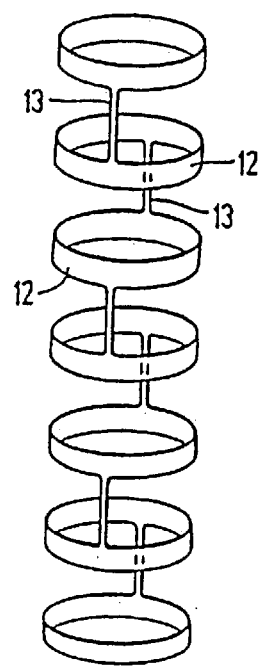
Figure 9:
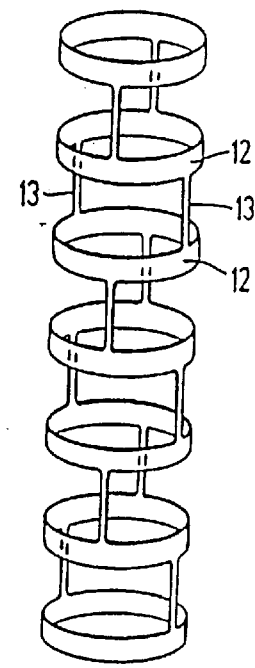

The number of undulations may also be varied to accommodate placement of interconnecting elements 13, e.g. at the peaks of the undulations or along the sides of the undulations as shown in FIGS. 5 and 11.

In keeping with the invention, and with reference to FIGS. 4 and 12–14, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32, and Y-shaped members 33, each having a different radius so that expansion forces are more evenly distributed over the various members.

Figure 13:
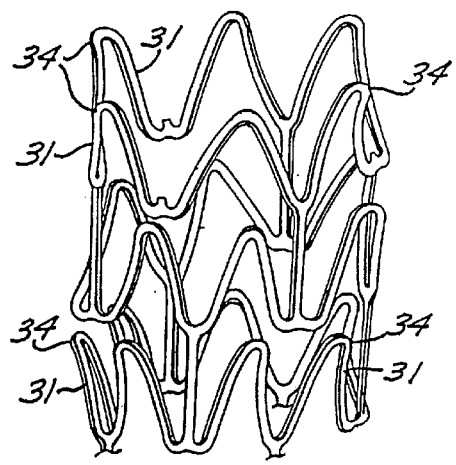
FIG. 13 is a perspective view of the stent of FIG. 4 after it is fully expanded depicting some members projecting radially outwardly.
Figure 14:
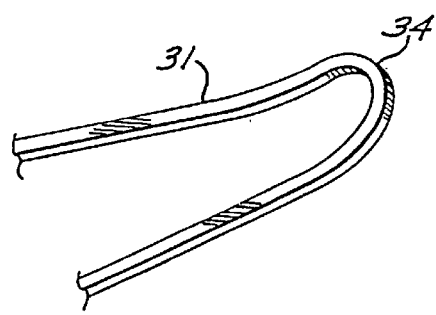
FIG. 14 is an enlarged, partial perspective view of one U-shaped member with its tip projecting outwardly after expansion.

As depicted in FIGS. 13 and 14, after cylindrical elements 12 have been radially expanded, outwardly projecting edges 34 are formed. That is, during radial expansion U-shaped members 31 will tip outwardly thereby forming outwardly projecting edges. These outwardly projecting edges provide for a roughened outer wall surface of stent 10 and assist in implanting the stent in the vascular wall by embedding into the vascular wall. In other words, outwardly projecting edges embed into the vascular wall, for example artery 15, as depicted in FIG. 3. Depending upon the dimensions of stent 10 and the thickness of the various members making up the serpentine pattern 30, any of the U-shaped members 31, W-shaped members 32, and Y-shaped members 33 can tip radially outwardly to form a projecting edge 34. It is most likely and preferred that U-shaped members 31 tip outwardly since they do not join with any connecting member 13 to prevent them from expanding outwardly.

The stent 10 of the present invention can be made in many ways. However, the preferred method of making the stent is to coat a thin-walled tubular member, such as stainless steel tubing, with a material which is resistive to chemical etchants, remove portions of the coating to expose underlying tubing which is to be removed but to leave coated portions of the tubing in the desired pattern for the stent so that subsequent etching will remove the exposed portions of the metallic tubing, but will leave relatively untouched the portions of the metallic tubing which are to form the stent. The coated portion of the metallic tube is in the desired shape for the stent. An etching process avoids the necessity of removing burrs or slag inherent in conventional or laser machining process. It is preferred to remove the etchant-resistive material by means of a machine-controlled laser as illustrated schematically in FIG. 6.

A coating is applied to a length of tubing which, when cured, is resistive to chemical etchants. "Blue Photoresist" made by the Shipley Company in San Jose, Calif., is an example of suitable commercially available photolithographic coatings. The coating is preferably applied by electrophoretic deposition.

To ensure that the surface finish is reasonably uniform, one of the electrodes used for the electrochemical polishing is a doughnut-shaped electrode which is placed about the central portion of the tubular member.

The tubing may be made of suitable biocompatible material such as stainless steel, titanium, tantalum, superelastic NiTi alloys and even high strength thermoplastic polymers. The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch. In the instance when the stent was plastic, it would have to be heated within the arterial site where the stent is expanded to facilitate the expansion of the stent. Once expanded, it would then be cooled to retain its expanded state. The stent may be conveniently heated by heating the fluid within the balloon or the balloon directly by a suitable system such as disclosed in a co-pending application Ser. No. 07/521,337, filed Jan. 26, 1990 entitled DILATATION CATHETER ASSEMBLY WITH HEATED BALLOON which is incorporated herein in its entirety by reference. The stent may also be made of materials such as superelastic NiTi alloys such as described in co-pending application Ser. No. 07/629,381, filed Dec. 18, 1990, entitled SUPERELASTIC GUIDING MEMBER which is incorporated herein in its entirety by reference. In this case the stent would be formed full size but deformed (e.g. compressed) into a smaller diameter onto the balloon of the delivery catheter to facilitate transfer to a desired intraluminal site. The stress induced by the deformation transforms the stent from a martensite phase to an austenite phase and upon release of the force, when the stent reaches the desired intraluminal location, allows the stent to expand due to the transformation back to the martensite phase.

Figure 6:
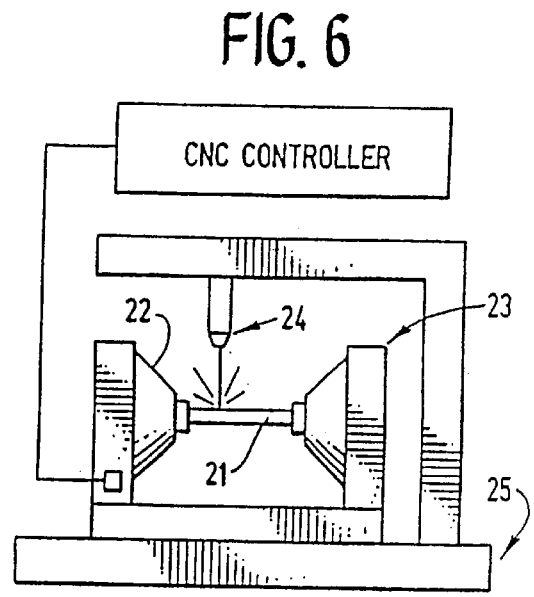
FIG. 6 is a schematic representation of equipment for selectively removing coating applied to tubing in the manufacturing of the stents of the present invention.

Referring to FIG. 6, the coated tubing 21 is put in a rotatable collet fixture 22 of a machine controlled apparatus 23 for positioning the tubing 21 relative to a laser 24. According to machine-encoded instructions, the tubing 21 is rotated and moved longitudinally relative to the laser 24 which is also machine controlled. The laser selectively removes the etchant-resistive coating on the tubing by ablation and a pattern is formed such that the surface of the tube that is to be removed by a subsequent chemical etching process is exposed. The surface of the tube is therefore left coated in the discrete pattern of the finished stent.

A presently preferred system for removing the coating on the tubing includes the use an 80-watt $CO_2$ laser, such as a Coherent Model 44, in pulse mode (0.3 mS pulse length); 48 mA key current and 48 W key power with 0.75 W average power, at 100 Hz; Anorad FR=20; 12.5 Torr; with no assist gas. Low pressure air is directed through the fine focus head to ensure that no vapor contacts the lens. The assist gas jet assembly on the laser unit may be removed to allow a closer proximity of the fine focus head and the collet fixture. Optimum focus is set at the surface of the tubing. Cured photo-resist coating readily absorbs the energy of the $CO_2$ wavelength, so that it can be readily removed by the laser. A coated 4-inch length of 0.06 inch stainless steel tubing is preferred and four stents can be patterned on the length of tubing. Three tabs or webs between stents provide good handling characteristics for the tubing after the etching process.

The process of patterning the resistive coating on the stent is automated except for loading and unloading the length of tubing. Referring again to FIG. 6 it may be done, for example, using a CNC-opposing collet fixture 22 for axial rotation of the length of tubing, in conjunction with a CNC X/Y table 25 to move the length of tubing axially relative to a machine-controlled laser as described. The entire space between collets can be patterned using the $CO_2$ laser set-up of the foregoing example. The program for control of the apparatus is dependent on the particular configuration used and the pattern to be ablated in the coating, but is otherwise conventional.

This process makes possible the application of present photolithography technology in manufacturing the stents. While there is presently no practical way to mask and expose a tubular photo-resist coated part of the small size required for making intravascular stents, the foregoing steps eliminate the need for conventional masking techniques.

After the coating is thus selectively ablated, the tubing is removed from the collet fixture 22. Next, wax such at ThermoCote N-4 is heated to preferably just above its melting point, and inserted into the tubing under vacuum or pressure. After the wax has solidified upon cooling, it is reheated below its melting point to allow softening, and a smaller diameter stainless steel shaft is inserted into the softened wax to provide support. The tubing is then etched chemically in a conventional manner. After cutting the tabs connecting the stents any surface roughness or debris from the tabs is removed. The stents are preferably electrochemically polished in an acidic aqueous solution such as a solution of ELECTRO-GLO #300, sold by the ELECTRO-GLO CO., Inc. in Chicago, Ill., which is a mixture of sulfuric acid, carboxylic acids, phosphates, corrosion inhibitors and a biodegradable surface active agent. The bath temperature is maintained at about 110–135 degrees F. and the current density is about 0.4 to about 1.5 amps per in.$^2$ Cathode to anode area should be at least about two to one. The stents may be further treated if desired, for example by applying a biocompatible coating.

While the invention has been illustrated and described herein in terms of its use as an intravascular stent, it will be apparent to those skilled in the art that the stent can be used in other instances such as to expand prostatic urethras in cases of prostate hyperplasia. Other modifications and improvements may be made without departing from the scope of the invention.

Other modifications and improvements can be made to the invention without departing from the scope thereof.

What is claimed is:

1. A longitudinally flexible stent for implanting in a body lumen, comprising:
   a plurality of cylindrical elements each having undulations, the cylindrical elements being expandable in the radial direction and interconnected to be generally aligned on a common longitudinal axis;
   a plurality of interconnecting elements for interconnecting the cylindrical elements, the interconnecting elements configured to interconnect only the cylindrical elements that are adjacent to each other;
   the undulations having peaks connected by a pair of sides; and
   at least one interconnecting element between adjacent cylindrical elements, the at least one interconnecting element being attached along one of the sides of the undulations.

2. The stent of claim 1, wherein the undulations include U-shaped members.

3. The stent of claim 2, wherein the U-shaped members are in an in-phase configuration.

4. The stent of claim 2, wherein the U-shaped members are in an out-of-phase configuration.

5. The stent of claim 1, wherein the stent is formed from a single piece of tubing.

6. The stent of claim 1, wherein at least a portion of the stent is coated with a biocompatible coating.

7. The stent of claim 1, wherein adjacent cylindrical elements are connected by at least two interconnecting elements.

8. The stent of claim 1, wherein adjacent cylindrical elements are connected by at least three interconnecting elements.

9. The stent of claim 1, wherein adjacent cylindrical elements are connected by at least four interconnecting elements.

* * * * *

UNITED STATES PATENT AND TRADEMARK OFFICE
CERTIFICATE OF CORRECTION

PATENT NO.    : 6,689,159 B2
DATED         : February 10, 2004
INVENTOR(S)   : Lilip Lau, William M. Hartigan and John J. Frantzen It is certified that error appears in the above-identified patent and that said Letters Patent is hereby corrected as shown below:

Title page,
Item [56], References Cited, insert the following:
U.S. PATENT DOCUMENTS

| | | |
|---|---|---|
| 4,130,904 A | 12/1978 | Whalen |
| 4,140,126 A | 2/1979 | Choudhyry |
| 4,159,719 A | 7/1979 | Haerr |
| 4,323,071 A | 4/1982 | Simpson |
| 4,387,952 A | 6/1983 | Slusher |

FOREIGN PATENT DOCUMENTS

| | |
|---|---|
| EP 221 570 A2 | 5/1987 |
| EP 380 668 | 10/1988 |
| EP 338 816 A | 10/1989 |
| EP 361 192 A | 4/1990 |
| EP 364 787 A | 4/1990 |
| EP 372 789 A3 | 6/1990 |
| EP 407 951 A | 1/1991 |
| EP 408 245 A1 | 1/1991 |
| EP 421 729 A2 | 4/1991 |
| EP 423 916 A1 | 4/1991 |
| EP 428 479 A1 | 5/1991 |
| EP 062 300 | 10/1992 |

Signed and Sealed this

Twenty-seventh Day of July, 2004

JON W. DUDAS
*Acting Director of the United States Patent and Trademark Office*